United States Patent
Yang et al.

(10) Patent No.: US 12,020,776 B2
(45) Date of Patent: Jun. 25, 2024

(54) OPTIMIZING PROTEINS USING MODEL BASED OPTIMIZATIONS

(71) Applicant: Flagship Pioneering Innovations VI, LLC, Cambridge, MA (US)

(72) Inventors: Kevin Kaichuang Yang, Arlington, MA (US); Jacob D. Feala, Franklin, MA (US); Maxim Baranov, Medford, MA (US); Brinda Monian, Medford, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 17/975,466

(22) Filed: Oct. 27, 2022

(65) Prior Publication Data

US 2023/0054552 A1 Feb. 23, 2023

Related U.S. Application Data

(63) Continuation of application No. PCT/US2021/029197, filed on Apr. 26, 2021.
(Continued)

(51) Int. Cl.
*G01N 33/48* (2006.01)
*G01N 33/50* (2006.01)
(Continued)

(52) U.S. Cl.
CPC .............. *G16B 15/30* (2019.02); *G06N 3/08* (2013.01); *G16B 15/20* (2019.02); *G16B 40/20* (2019.02)

(58) Field of Classification Search
CPC ........ G16B 15/30; G16B 15/20; G16B 40/20; G06N 3/08
See application file for complete search history.

(56) References Cited

U.S. PATENT DOCUMENTS

2017/0199961 A1* 7/2017 Yelensky ............ A61K 39/0011
2018/0319850 A1* 11/2018 Payne .................... C12N 15/86

FOREIGN PATENT DOCUMENTS

WO 2021/222121 A1 11/2021

OTHER PUBLICATIONS

Phloyshisut et al. MHCSeqNet: a deep neural network model for universal MHC binding prediction. BMC Bioinformatics, vol. 20, article 270, 10 pages. (Year: 2019).*

(Continued)

*Primary Examiner* — Russell S Negin
(74) *Attorney, Agent, or Firm* — Hamilton, Brook, Smith & Reynolds, P.C.

(57) ABSTRACT

Humanizing proteins can be a laborious process, often involving trial and error or other non-systematic methods. To improve humanization, neural networks can be employed to generate new protein sequences having higher probabilities of being humanized. In an embodiment, a method includes evaluating the immunogenicity of a sampling of protein sequences. The method can include weighting the sampling of protein sequences from the generative model according to an estimated probability of a particular generated protein sequence having a deviation in immunogenicity than a particular percentile of immunogenicity of the sampling of protein sequences. The method can further include generating a protein sequence weighted sampling of protein sequences. The generated protein sequence representing a protein has an altered immunogenicity. Such a generated protein has a higher likelihood of being humanized.

22 Claims, 9 Drawing Sheets

Related U.S. Application Data

(60) Provisional application No. 63/015,812, filed on Apr. 27, 2020.

(51) Int. Cl.
    *G06N 3/08*     (2023.01)
    *G16B 15/20*     (2019.01)
    *G16B 15/30*     (2019.01)
    *G16B 40/20*     (2019.01)

(56) References Cited

OTHER PUBLICATIONS

Cho et al. On the properties of neural machine translation: encoder-decoder approaches. arXiv1409:1259v2, 9 pages. (Year: 2014).*

Rothbard et al. Interactions between immunogenic peptides and MHC proteins. Annu. Rev. Immunol., vol. 9, pp. 527-565. (Year: 1991).*

Safdari et al. Antibody humanization methods—a review and update. Biotechnology and Genetic Engineering Reviews, vol. 29, pp. 175-186. (Year: 2013).*

Amimeur Tileli et al: "Designing Feature-Controlled Humanoid Antibody Discovery Libraries Using Generative Adversarial Networks", bioRxiv, Apr. 23, 2020 (Apr. 23, 2020).

David H Brookes et al: "Conditioning by adaptive sampling for robust design", arxiv .org, Cornell University Li bra ry, 201 Olin Li bra ry Cornell University Ithaca, NY 14853, Jan. 29, 2019 (Jan. 29, 2019).

David H Brookes et al: "Design by adaptive sampling", arxiv .org, Cornell University Li bra ry, 201 Olin Li bra ry Cornell University Ithaca, NY 14853, Oct. 8, 2018 (Oct. 8, 2018).

International Search Report and Written Opinion received for PCT Patent Application No. PCT/US21/29197, dated Jul. 23, 2021, 12 pages.

International Preliminary Report on Patentability received for PCT Patent Application No. PCT/US21/29197, dated Nov. 10, 2022, 11 pages.

* cited by examiner

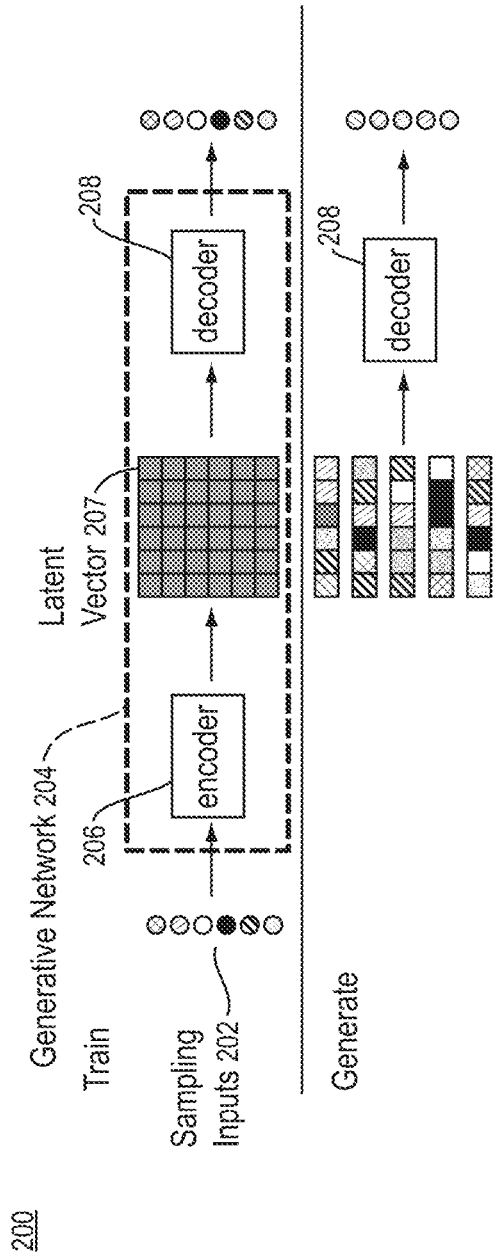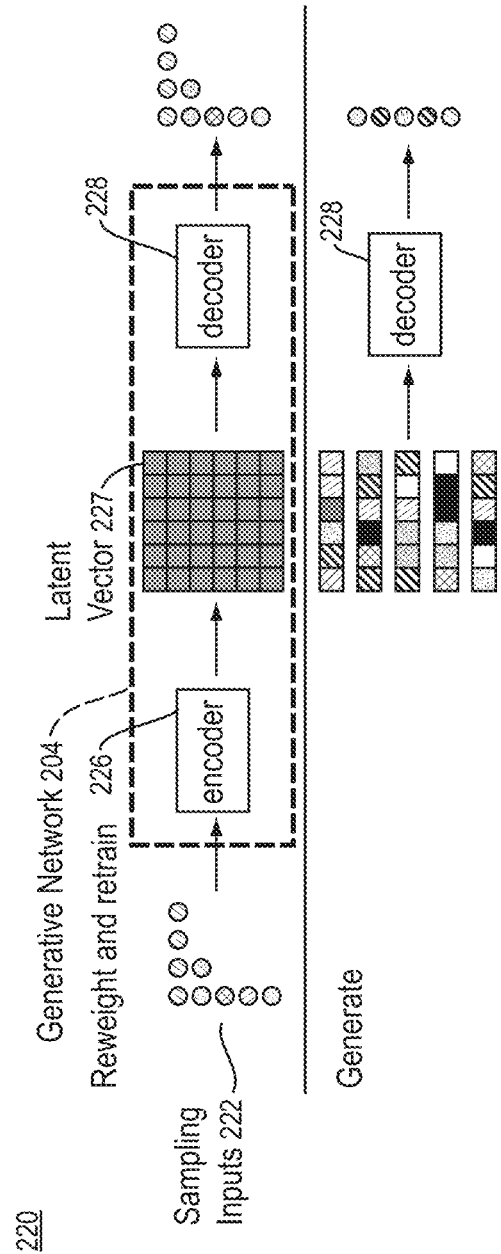

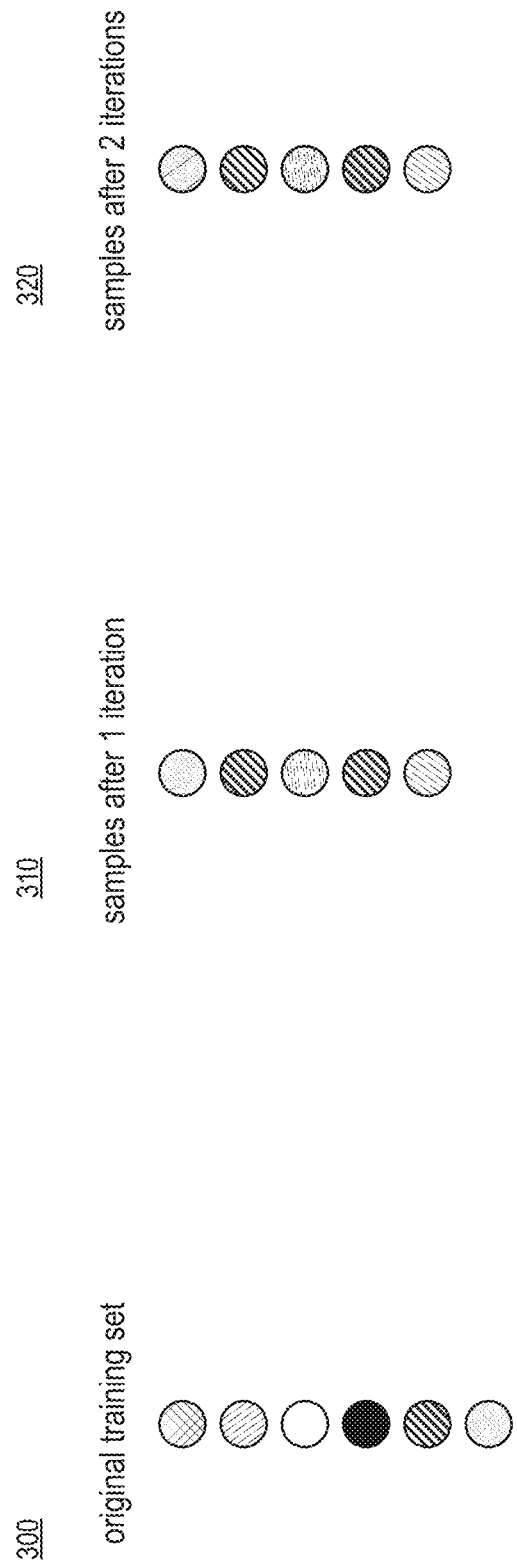

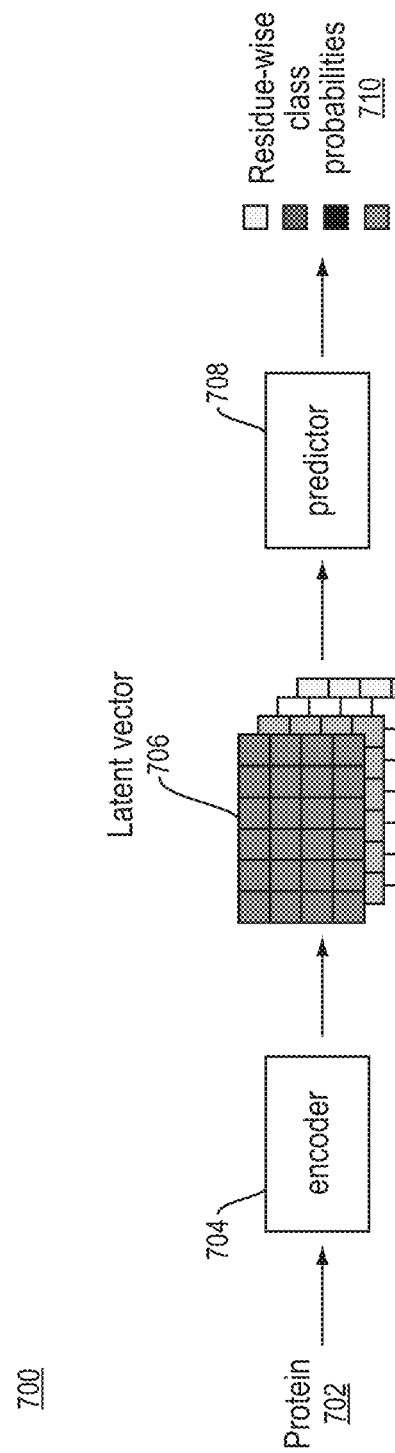

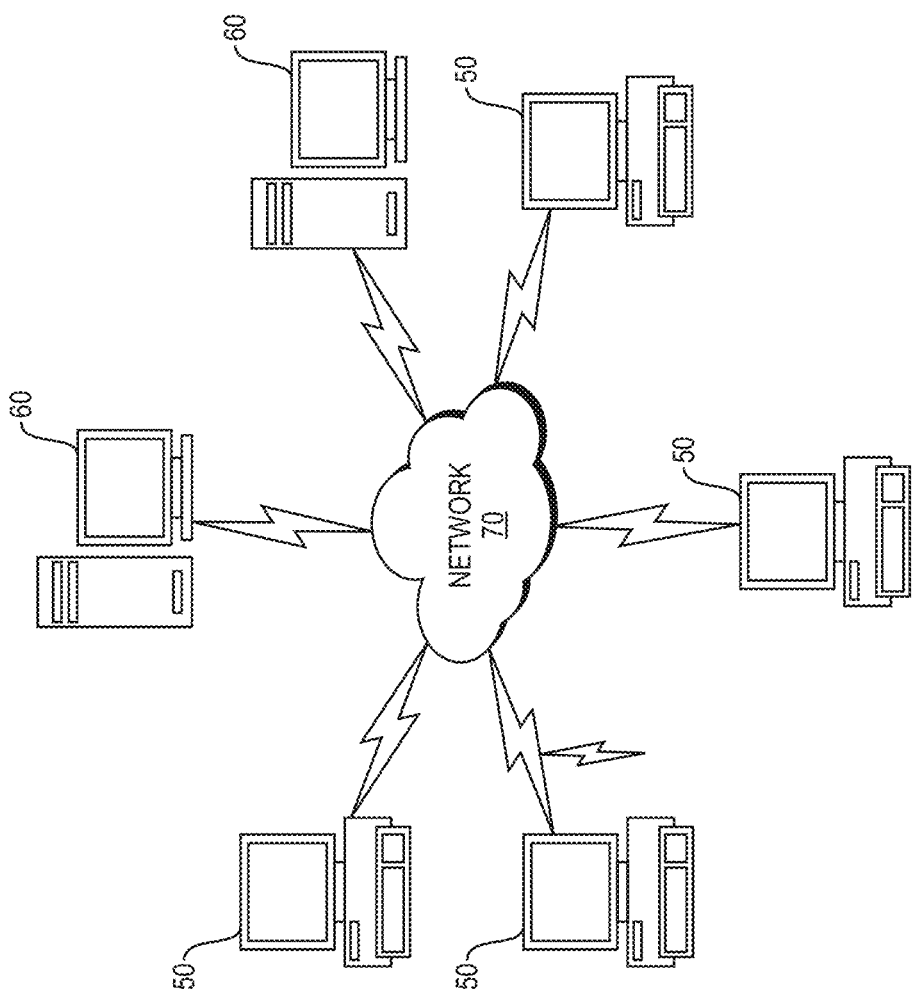

OPTIMIZING PROTEINS USING MODEL BASED OPTIMIZATIONS

RELATED APPLICATIONS

This application is a continuation of International Application No. PCT/US2021/029197, which designated the United States and was filed on 26 Apr. 2021, published in English, which claims the benefit of U.S. Provisional Application No. 63/015,812, filed on Apr. 27, 2020. The entire teachings of the above applications are incorporated herein by reference.

BACKGROUND

Humanization is a process of modifying the amino acid sequence of a protein from a non-human source (e.g., a mouse monoclonal antibody) to render the modified, or humanized, protein less immunogenic when introduced into a human subject. It is often desirable to preserve one or more properties (e.g., an enzymatic activity, a target binding affinity) of the parental non-human protein in the humanized protein that results from the humanization process. Therefore, processes for determining humanized sequences of a non-human protein that reduce or eliminate immunogenicity while preserving one or more desired functions of the non-human protein are useful.

SUMMARY

In an embodiment, a method includes evaluating the immunogenicity of a sampling of protein sequences from a generative model. The generative model preserves the desired function. The method can include retraining the generative model by weighting the sampling of protein sequences from the generative model according to an estimated probability of a particular generated protein sequence having a deviation in immunogenicity of a particular percentile of immunogenicity of the sampling of protein sequences. The method can further include generating a protein sequence using the retrained generative model. The generated protein sequence representing a protein predicted to have an altered immunogenicity.

In an embodiment, the method can produce one or more protein sequences using the retrained generative model.

In an embodiment, a method of generating a sequence of a protein predicted to have altered immunogenicity compared to a sampling of protein sequences, the protein having a desired function. The method can include evaluating the immunogenicity of a sampling of protein sequences. The method can further include selecting a set of protein sequences from the sampling by weighting the sampling of protein sequences according to an estimated probability of a particular generated protein sequence having a deviation in immunogenicity of a particular percentile of immunogenicity of the sampling of protein sequences. The method further includes generating a protein sequence based on the selected set of protein sequences, the protein sequence representing a protein predicted to have an altered immunogenicity.

In an embodiment, the above method can be executed within a system or its steps stored on a non-transitory computer readable medium, such that when the steps are loaded to and executed by a processor, the processor performs the above steps.

In an embodiment, an isolated protein sequence comprising an amino acid sequence that differs from a sample of amino acid sequences by at least one amino acid addition, deletion, or substitution relative to the sample generated by the preceding methods.

An aspect of the present disclosure relates to a method of generating a sequence of a protein predicted to have altered immunogenicity compared to a sampling of protein sequences, the protein having a desired function. The method may, at least in part or entirely, relate to a computer-implemented method. The method comprises evaluating the immunogenicity of a sampling of protein sequences. For example, the immunogenicity of the sampling of protein sequences may be evaluated based on or from a generative model, wherein the generative model may be configured to preserve a desired function. The method further comprises selecting a set of protein sequences from the sampling by weighting the sampling of protein sequences according to an estimated probability of a particular generated protein sequence having a deviation in immunogenicity of a particular percentile of immunogenicity of the sampling of protein sequences. The method further comprises generating a protein sequence based on the selected set of protein sequences, the protein sequence representing a protein predicted to have an altered immunogenicity.

In an embodiment, the sampling of protein sequences is from a generative model and the generative model is configured to preserve the desired function. The method may further comprise retraining the generative model based on the selected set of protein sequences, wherein generating the protein sequence is based on the retrained generative model that is retrained based on the selected set of protein sequences.

In an embodiment, the generative model includes at least one encoder neural network and at least one decoder neural network.

As used herein the "encoder neural network" (also referred to as encoder in the following) and the "decoder neural network" (also referred to as decoder in the following) may generally refer to one or more functional and/or structural components parts, sections, stages or modules of the generative model (also referred to as generative network in the following).

The encoder neural network may, for example, be configured to process an input, such as a sampling input, into an intermediate output. The encoder neural network may further be configured to provide and/or pass the intermediate output to the decoder neural network. The decoder neural network may be configured to reconstruct the input based on processing the intermediate output provided by the encoder neural network.

In an example, the encoder neural network may be configured to map a sampling input to a latent vector. Alternatively or additionally, the decoder neural network may be configured to estimate, reconstruct and/or compute the sampling input from the latent vector to produce an output.

Generally, the generative model, the encoder neural network and/or the decoder neural network can be implemented in hardware and software. Alternatively or additionally, the generative model, the encoder neural network and/or the decoder neural network can include one or processors for data processing.

In an embodiment, the method further comprises retraining the generative model two or more iterations, wherein each iteration includes: a) evaluating the immunogenicity of a sampling of protein sequences generated by the retrained generative model, and b) further retraining the generative model by weighting the sampling of protein sequences generated by the retrained generative model according to their evaluated immunogenicity in the retraining.

In an embodiment, retraining the generative model two or more iterations includes retraining the generative model multiple iterations until convergence. This may include minimizing and/or optimizing one or more functions, one or more weights, one or more parameters and/or one or more characteristics of the generative model.

In an embodiment, the sampling of protein sequences is unique from any protein sequences present in a training set of protein sequences used to train the generative model.

A further aspect of the present disclosure relates to a method of generating a sequence of a protein predicted to have altered immunogenicity compared to a sampling of protein sequences, the protein having a desired function. The method may, at least in part or entirely, relate to a computer-implemented method. The method comprises evaluating the immunogenicity of a sampling of protein sequences, weighting the sampling of protein sequences according to an estimated probability of a particular generated protein sequence having a deviation in immunogenicity of a particular percentile of immunogenicity of the sampling of protein sequences, resulting in a first weighted sampling of protein sequences, evaluating the immunogenicity of a sampling of protein sequences using first sampling of protein sequences, reweighting the sampling of protein sequences from the first weighted sampling of protein sequences evaluated for immunogenicity according to their evaluated immunogenicity, resulting in a second weighted sampling of protein sequences, and generating a protein sequence from the second weighted sampling of protein sequences, the protein sequence representing a protein predicted to have an altered immunogenicity.

In an embodiment, the method further comprises providing a generative model that preserves the desired function, the generative model comprising an encoder neural network and a decoder neural network.

In an embodiment, evaluating the immunogenicity of the sampling of protein sequences further includes evaluating the immunogenicity from a generative model, wherein the generative model preserves the desired function, the generative model further comprising an encoder neural network and a decoder neural network.

In an embodiment, the sampling of protein sequences does not comprise any protein sequences present in a training set of protein sequences used to weight the first weighted sampling of protein sequences.

In an embodiment, the first weighted sampling of protein sequences does not comprise any sequences present in a training set of protein sequences used to weight the first weighted sampling of protein sequences.

In an embodiment, the method further comprises iterating the steps of evaluating the immunogenicity of a sampling of protein sequences and providing a second weighted sampling of protein sequences.

In an embodiment, the immunogenicity is evaluated using the predicted affinity of k-mers of a subject sequence for a MHC molecule.

In an embodiment, k is greater than or equal to 5 and less than or equal to 13.

In an embodiment, the predicted affinity for a k-mer of a subject sequence for the MHC molecule is evaluated by one or more of MHCFlurry, NetMHCpan, or NetMHCIIpan.

In an embodiment, the method further comprises combining the predicted affinity of k-mers by at least one of (a) the reciprocal of the sum of the reciprocal of each predicted affinity of k-mers, and (b) the lowest predicted affinity of the k-mers.

In an embodiment, the immunogenicity of the sampling of protein sequences from the first weighted sampling of protein sequences or second weighted sampling of protein sequences is evaluated experimentally.

In an embodiment, the altered immunogenicity is reduced immunogenicity.

In an embodiment, the reduced immunogenicity is reduced affinity for a human MHC, including at least one of human MHC I, such as human MHC I encoded by allele HLA-A0201, and MHC II.

In an embodiment, the altered immunogenicity is increased immunogenicity.

In an embodiment, the increased immunogenicity is increased affinity for a human MHC, such as human MHC I, such as human MHC I encoded by allele HLA-A0201.

In an embodiment, the desired function is selected from enzymatic activity, target binding affinity (other than an MHC), thermal stability, solubility, size of protein, intracellular location of protein, activation of a cellular signaling pathway or gene expression program, and expression level.

In an embodiment, the enzymatic activity is asparaginase activity.

In an embodiment, immunogenicity is evaluated using residue-wise predictions of a relative likelihood for MHC II to bind to the protein predicted to have the altered immunogenicity.

In an embodiment, a candidate model accepts an amino acid sequence as input and outputs one or more residue-wise predictions of relative likelihood for MHCII to bind to a peptide containing each residue.

In an embodiment, the method further comprises evaluating the model based on a false negative rate and a model accuracy rate.

In an embodiment, the estimated probability is a likelihood of WIC II presentation, and the likelihood is based on both a probability of peptide presentation of WIC-associated peptide proteomics (MAPPS).

In an embodiment, the first weighted sampling of protein sequences is used to provide a first updated generative model by updating a generative model, and second weighted sampling of protein sequences is used to provide a second updated generative model that retrains the first updated generative model.

A further aspect of the present disclosure method of generating a sequence of a protein predicted to have altered immunogenicity compared to a sampling of protein sequences, the protein having a desired function. The method may, at least in part or entirely, relate to a computer-implemented method. The method comprises providing a generative model that preserves the desired function, the generative model comprising an encoder neural network and a decoder neural network, evaluating the immunogenicity of a sampling of protein sequences from a generative model, wherein the generative model preserves the desired function, the generative model further comprising an encoder neural network and a decoder neural network, providing a first updated generative model by retraining the generative model by weighting the sampling of protein sequences from the generative model according to an estimated probability of a particular generated protein sequence having a deviation in immunogenicity of a particular percentile of immunogenicity of the sampling of protein sequences, evaluating the immunogenicity of a sampling of protein sequences using the first updated generative model, providing a second updated generative model by retraining the first updated generative model by weighting the sampling of protein sequences from the first updated generative model evaluated for immunogenicity according to their evaluated immunogenicity in the retraining, and generating a protein sequence from the further updated generative model, the protein sequence representing a protein predicted to have an altered immunogenicity.

In an embodiment, the generative model is a variational auto encoder (VAE).

In an embodiment, the generative model was trained using a set of naturally occurring sequences predicted to have the desired function.

In an embodiment, the encoder neural network and decoder neural network were trained to minimize the negative log-likelihood of a reconstruction of an input the input to the encoder by the output of the decoder.

In an embodiment, the encoder neural network and decoder neural network were trained to minimize the Kullback-Leibler-divergence (KLD) between the encoder and Normal (0,1).

In an embodiment, the encoder neural network and decoder neural network are at least one of a feed-forward neural network, convolutional neural network, and recurrent neural network.

In an embodiment, the encoder neural network and decoder neural network employ at least two hidden layers.

In an embodiment, the immunogenicity of a sampling of protein sequences from the generative model or updated generative model is evaluated by a neural network In an embodiment, the neural network evaluates the immunogenicity of the sampling of protein sequences by an oracle outputting a value.

In an embodiment, the oracle further outputs an uncertainty.

In an embodiment, the generative model can include any of the following architectures: feedforward multilayer perceptrons (MLP), convolutional, and transformer, and wherein the generative model can be provided with and without unsupervised pretraining.

In an embodiment, providing the generative model includes training the generative model for three cycles of five epochs per cycle, wherein each epoch follows a one-cycle annealing schedule.

A further aspect of the present disclosure to the use of a generative model for generating a sequence of a protein predicted to have altered immunogenicity compared to a sampling of protein sequences.

A further aspect of the present disclosure relates to an isolated protein sequence and/or a use thereof, the isolated protein sequence comprising an amino acid sequence that differs from a sample of amino acid sequences by at least one amino acid addition, deletion, or substitution relative to the sample generated by one or more methods according to one or more aspects, embodiments, examples and exemplary embodiments described hereinabove and hereinbelow.

A further aspect of the present disclosure relates to a system for generating a sequence of a protein predicted to have altered immunogenicity compared to a sampling of protein sequences, the protein having a desired function. The system comprises at least one processor, and a memory with computer code instructions stored thereon, the processor and the memory, with the computer code instructions, being configured to cause the system to:

evaluate the immunogenicity of a sampling of protein sequences, select a set of protein sequences from the sampling by weighting the sampling of protein sequences according to an estimated probability of a particular generated protein sequence having a deviation in immunogenicity of a particular percentile of immunogenicity of the sampling of protein sequences, and generate a protein sequence based on the selected set of protein sequences, the protein sequence representing a protein predicted to have an altered immunogenicity.

A further aspect of the present disclosure to the use of a system for generating a sequence of a protein predicted to have altered immunogenicity compared to a sampling of protein sequences, the protein having a desired function.

It is emphasized that any feature, function, step, advantage, and/or technical effect described hereinabove and hereinbelow with reference to one aspect of the present disclosure equally applies to any other aspect of the present disclosure. In particular, it is emphasized that any feature, function, step, advantage, and/or technical effect described hereinabove and hereinbelow with respect to one or more methods according to one or more aspects of the present disclosure, equally applies to the system described hereinabove and hereinbelow.

A further aspect of the present disclosure relates to a non-transitory computer readable medium having instructions stored thereon for generating a sequence of a protein predicted to have altered immunogenicity compared to a sampling of protein sequences, the protein having a desired function, the instructions configured to, when loaded and executed by a processor, cause the processor to evaluate the immunogenicity of a sampling of protein sequences, to select a set of protein sequences from the sampling by weighting the sampling of protein sequences according to an estimated probability of a particular generated protein sequence having a deviation in immunogenicity of a particular percentile of immunogenicity of the sampling of protein sequences, and to generate a protein sequence based on the selected set of protein sequences, the protein sequence representing a protein predicted to have an altered immunogenicity.

A further aspect of the present disclosure relates to a method of generating a sequence of a protein predicted to have altered immunogenicity compared to a sampling of protein sequences, the protein having a desired function. The method comprises evaluating the immunogenicity of a sampling of protein sequences from a generative model, the generative model preserving the desired function, retraining the generative model by weighting the sampling of protein sequences from the generative model according to an estimated probability of a particular generated protein sequence having a deviation in immunogenicity of a particular percentile of immunogenicity of the sampling of protein sequences, and generating a protein sequence using the retrained generative model, the protein sequence representing a protein predicted to have an altered immunogenicity.

A further aspect of the present disclosure relates to a method of training a generative model based on a selected set of protein sequences for use in a method or a system according to one or more aspects of the present disclosure, as described hereinabove and hereinbelow.

In an embodiment, the trained generative model is further retrained based on the selected set of protein sequences, wherein generating the protein sequence is based on the retrained generative model that is retrained based on the selected set of protein sequences.

A further aspect of the present disclosure relates to a protein sequence generated and/or obtained by or based on any one or more methods or systems described hereinabove and hereinbelow with reference to one or more aspects of the present disclosure.

Any feature, function, step, and/or element described hereinabove and hereinbelow with reference to one aspect, an embodiment of an aspect, and/or an example of an aspect of the present disclosure can be combined with any other aspect, any embodiment of any other aspect, and/or any example of any other aspect of the present disclosure, as described hereinabove and hereinbelow.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 2A-B are diagrams illustrating an embodiment of a simplified example of the present disclosure.

FIGS. 3A-C are diagrams illustrating, respectively, the original training set, the samples after one iteration of setting Q to be a redder color and the samples after two iterations of setting Q to be a redder color according to an exemplary embodiment of the present disclosure.

FIG. 7 is a block diagram illustrating an example embodiment of the present disclosure.

FIG. 8 illustrates a computer network or similar digital processing environment in which embodiments of the present disclosure may be implemented.

DETAILED DESCRIPTION

A description of example embodiments follows.

Figure 1:
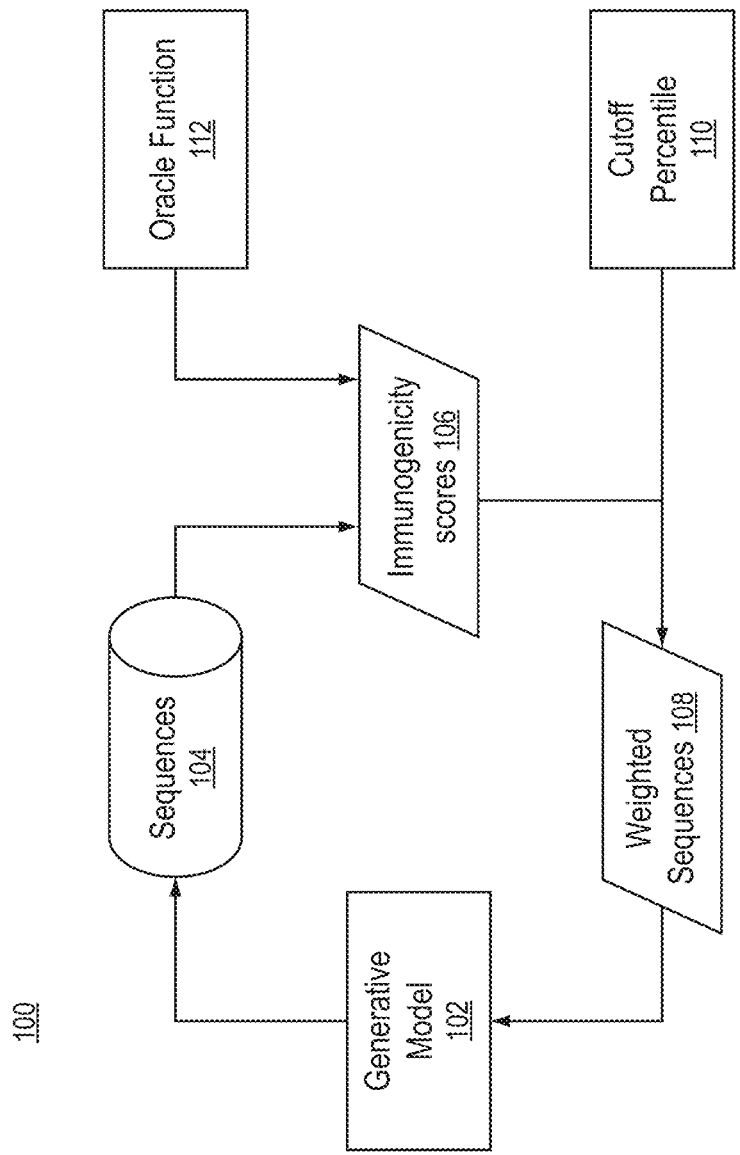
FIG. 1 is a diagram illustrating an example embodiment of the present disclosure.

FIG. 1 is a diagram 100 illustrating an example embodiment of the present disclosure. In general, the method is model based optimization for methods that starting with a population (e.g., of proteins) and improving the population iteratively. In an example embodiment, the present disclosure describes methods to generate humanized proteins using design by adaptive sampling.

A generative model 102, initially trained by a set of protein sequences, generates sequences 104. The generated sequences 104 preserve a desired function of the training set of protein sequences. An oracle function 112 can determine a probability distribution that each sequence of the sequences 104 has a property of interest, such as immunogenicity. The immunogenicity scores 106 are then weighted based on the desirability of the scores. In most cases, a lower immunogenicity score is more desirable. However, a person having ordinary skill in the art can recognize that in certain embodiments, the immunogenicity scores can be expressed in a non-traditional manner, such that higher scores may be desirable. A cutoff percentile 110 removes sequences that are scored as having a probability above a Qth percentile, where Q is set by a user, for the property of interest. The remaining weighted sequences 108 therefore only include those having a probability above the Qth percentile of the property of interest, or in this case, immunogenicity. Then, these weighted sequences 108 retrain the generative model 102.

The generative model 102 begins another iteration of the above described sequence. Each iteration improves the sequences 104 generated by the generative model 102, where the improvement produces more sequences having a probability above the Qth percentile for the quality being measured (e.g., immunogenicity). A person having ordinary skill in the art can understand that the iterations can continue until the immunogenicity scores 106 converge within a particular threshold designated to be stability of the solution.

The goal for the oracle is to score a protein for its likelihood to be processed into peptides and presented on MHC II molecules. The rationale for this was that MHC II presentation is a necessary step for T-cell priming, which in turn is usually required for an immune response. Thus, predicted likelihood of MHC II presentation may be a useful correlate of protein immunogenicity. The oracle is designed to generate a protein-wide MHC II presentation score, given the predicted probabilities of protein-wide MHC II presentation from an additional machine learning model. A person of ordinary skill in the art can recognize that "Improved prediction of MHC II antigen presentation through integration and motif deconvolution of mass spectrometry MHC eluted ligand data" by Birkir Reynisson discloses an MHC II predictor, and is incorporated by reference in its entirety.

In addition to the above known oracle models, a novel oracle is disclosed below. The novel oracle is a predictive model that assesses the likelihood of MHC II presentation. To train a predictive model assessing the likelihood of MHC II presentation, datasets of protein sequences and their associated MHC II-presented peptides, if any, are obtained. While methods exist for assaying the likelihood of peptide presentation and/or MHC binding, a sensitive method is desired that is both maximally unbiased for specific peptides and scalable to many proteins. Therefore, in some embodiments, datasets collected via MAPPs (MHC-associated peptide proteomics) are employed. MAPPs are a method in which peptides that are presented on MHC molecules on cells are eluted and characterized via mass spectrometry at high throughput. These peptides can be from endogenous proteins or foreign proteins (e.g., a protein administered to a mouse or a protein present in cell culture medium). For the purposes of the present disclosure, both types of data are valuable, as the present method uses a general model able to predict, for example, MHC II presentation for a diversity of proteins.

Consider all major MAPPs studies to date that assessed peptide presentation on murine cells via MHC II. These studies include data from C57BL/6 mouse cells, with a smaller contribution of data from Balb/c mouse cells. Both datasets are incorporated into the predictive model for assessing the likelihood of MHC II presentation, with the assumption that MHC II binding can be different across mouse strains due to differences in MHC II alleles, but that proteolytic cleavage and processing are likely shared, and that thus there can be some shared signal of peptide presentation that could be done using all data together. The datasets used can include Sofron, A. et al. (2015), "High-resolution analysis of the murine MHC class II immunopeptidome." Eur J Immunol, 46(2), 319-328 (hereinafter "Sofron"), Fugmann, T. et al. (2017). "The MHC class II immunopeptidome of lymph nodes in health and in chemically induced colitis." J Immunol, 198(3): 1357-1364 (hereinafter "Fugmann"), and Graham, D. B. et al. (2018). Antigen discovery and specification of immunodominance hierarchies for MHCII-restricted epitopes. Nat Medicine, 24, 1762-1778 (hereinafter "Graham"). In other embodiments, additional data sets, optionally including different MHCs, or other cell-surface immune receptors, can be used—either in addition or as alternatives.

Each dataset includes a list of peptides detected under various conditions and a "most likely" UniProt accession number for each peptide. This accession number is used to retrieve the protein sequences corresponding to each peptide. Entries are filtered to exclude any peptides that did not have an exact match anywhere in the protein sequence, or whose protein sequence was longer than 10,000 amino acids. Finally, a start and end site for each peptide within each protein is determined.

In this setting, the problem can be formulated naturally as a position-wise classification learning task. Residues are assigned one of three class labels according to how many times the residue has been associated with a peptide observed to have exhibited binding to, optionally, MHCII (class 0: no peptides, class 1: (fringe residue) one peptide, class 2: (core residue)>=one peptide). This formulation naturally normalizes for protein expression, which has been found to be the most predictive attribute for MHC presentation in MAPPs data, since each protein provides its own negative controls in the form of peptides not presented. To account for false negative peptides from low-expressed proteins, the data may be filtered for peptides having at least some threshold of counts in the mass spectrometry data. Other peptide binding data, such as in-vitro MHC ligand binding affinities, are easily incorporated into a residue-based classification.

Figure 4:
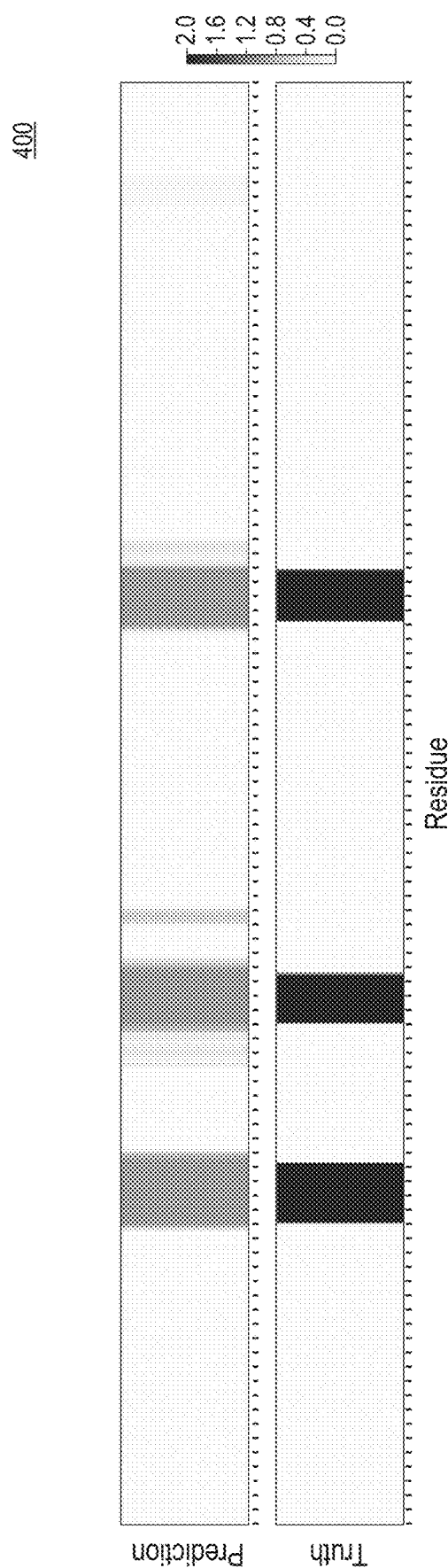
FIG. 4 is a graph illustrating an example model output and a corresponding ground truth according to an exemplary embodiment of the present disclosure.

Candidate models accept amino acid sequence as input and output residue-wise predictions of relative likelihood for an MHCII to bind to a peptide containing each residue. FIG. 4 is a graph illustrating an example model output and a corresponding ground truth.

With intended downstream applications of the model in mind, key metrics for this task were false negative rate (FN/(FN+TN)) and accuracy.

Figure 5A:
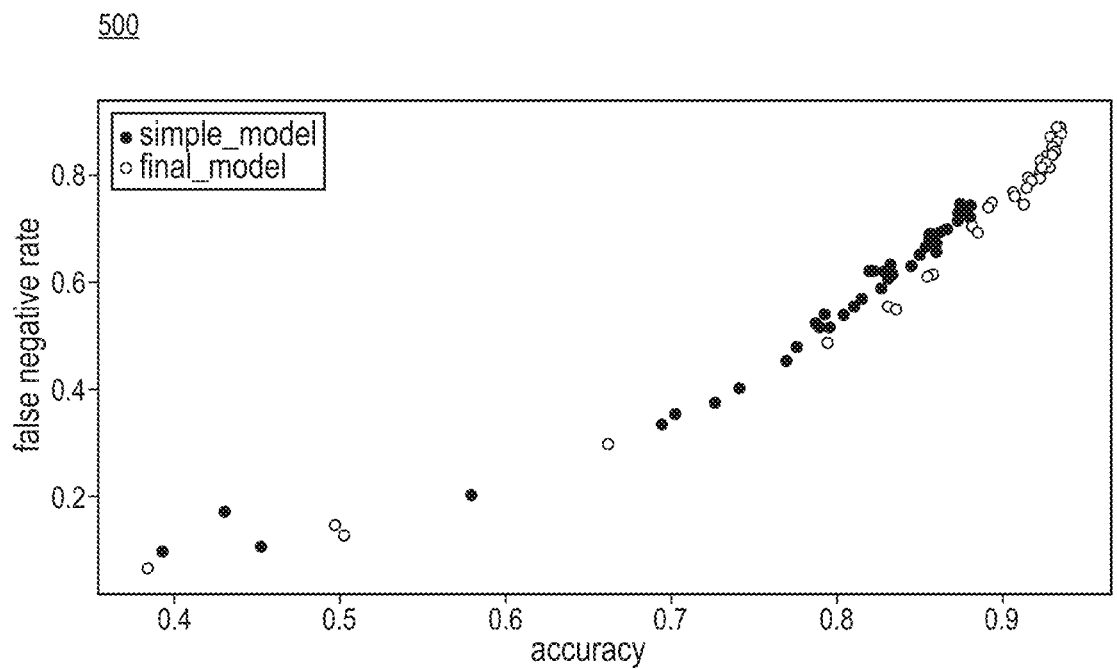
FIG. 5A is a graph illustrating that a shallow CNN underperforms to the final transformer architecture that was selected on homology-based splits according to an exemplary embodiment of the present disclosure.
Figure 5B:
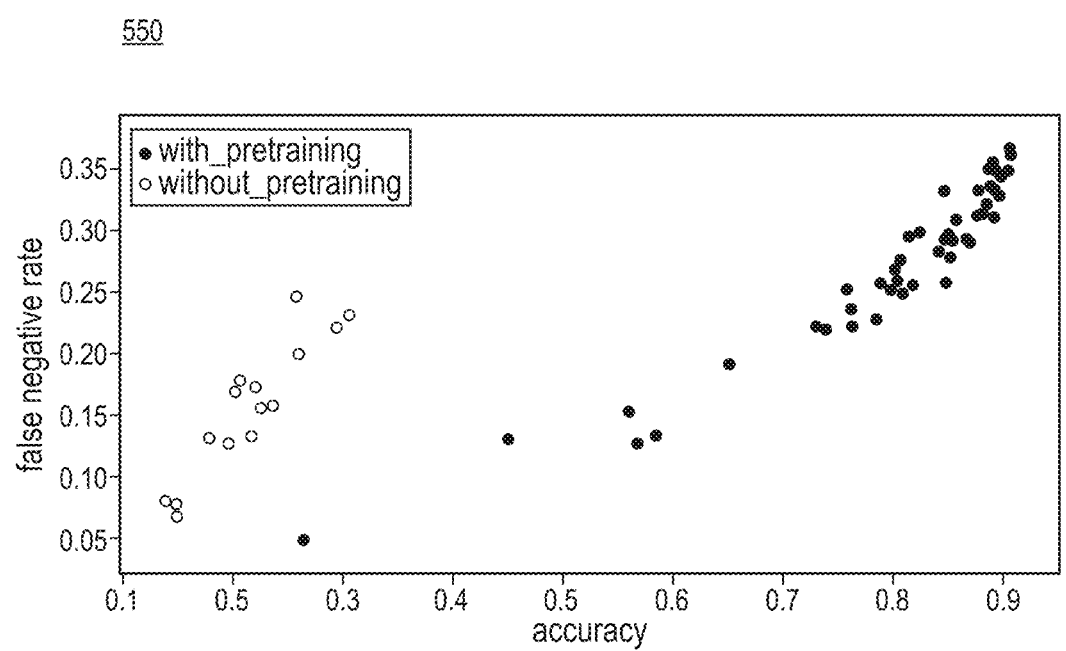
FIG. 5B is a graph illustrating the significant benefit of leveraging unsupervised pretraining with the transformer architecture according to an exemplary embodiment of the present disclosure.

Models are assessed by comparing maximal accuracy at a given false negative rate and minimum false negative rate at a given accuracy. FIG. 5A is a graph illustrating that a shallow convolutional neural network (CNN) underperforms to the final transformer architecture that was selected on homology-based splits, in other words, training on protein sequences unrelated by sequence homology to the test set held out for evaluation. FIG. 5B is a graph 550 illustrating the significant benefit of leveraging unsupervised pretraining on all available protein sequences in Uniprot with the transformer architecture.

Figure 6A:
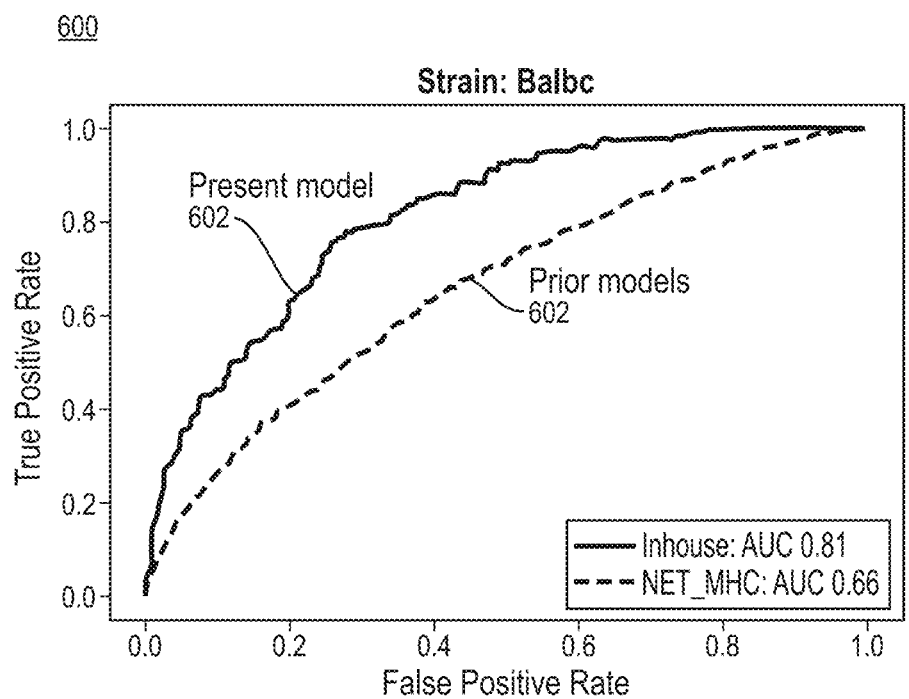
FIGS. 6A-B are graphs illustrating false positive and true positive rates for BALBC and C57BL6 strains, respectively, according to an exemplary embodiment of the present disclosure.
Figure 6B:
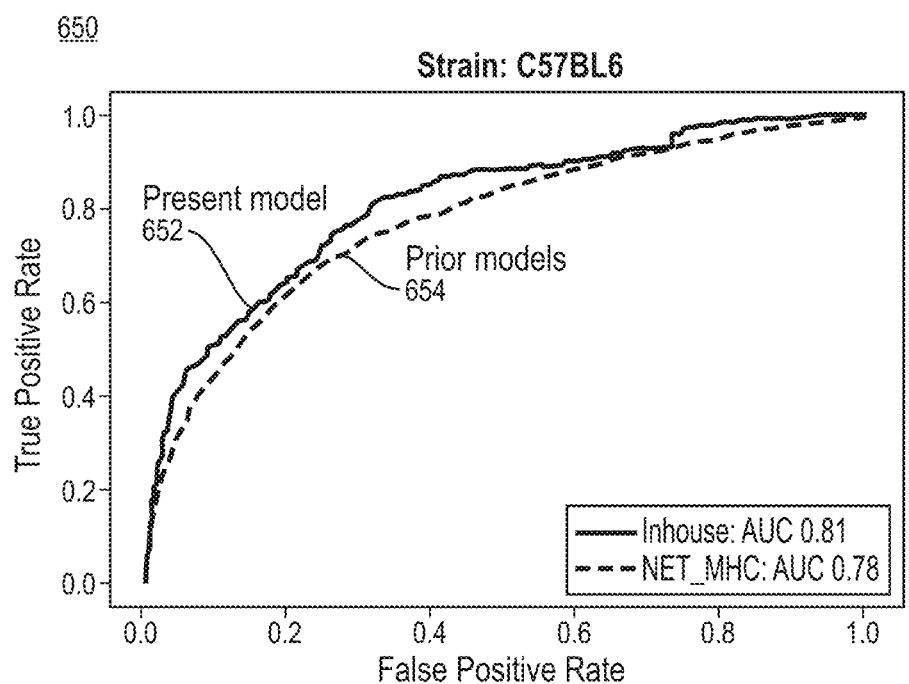

A residue-wise classifier gives rise to a peptide-level classifier in a natural way by considering average output across contiguous subsequences of a fixed length across a protein. This allows for computation of peptide-level accuracies which in turn allows for direct comparison with industry standard MHCII binding predictors. FIGS. 6A-B are graphs 600 and 650 illustrating false positive and true positive rates for Balbc and C57BL6 strains, respectively. Graph 600 illustrates the false positive rate against the true positive rate for the present model 602 and previous models 604 for the Balbc strain. Similarly, Graph 650 illustrates the false positive rate against the true positive rate for the present model 652 and prior models 654 for the C57BL6 strain.

A variety of architectures (feedforward multilayer perceptrons (MLP), convolutional, transformer) with and without unsupervised pretraining were trained/evaluated according to these metrics. Final hyperparameters are tuned by hand.

FIG. 7 is a block diagram illustrating an example embodiment of the present disclosure. The final production architecture is a two-layer feedforward MLP classifier/predictor 708. The predictor 708, based on latent vector(s) 707, outputs logits corresponding to one of three classes for each residue in the input protein, as shown by the residue-wise class probabilities. The predictor 708 is stacked on top of a twelve-layer attentional encoder 704 (e.g., a transformer). The encoder/transformer 704 is instantiated with pretrained weights and fine-tuned to leverage unsupervised pretraining.

Residues in the dataset are labeled as class 2 if the position on that protein appeared more than one peptide across all assays surveyed, class 1 if the position occurred in only one peptide, otherwise class 0. Classes 0, 1, 2 are weighted 1.037, 10, 100 respectively in the loss function calculation. The skilled artisan will readily appreciate that alternative weightings can be employed. In certain embodiments, the model is trained for three cycles of five epochs per cycle, each following a one-cycle annealing schedule with discriminative learning rates of 1e−6 and 1e−5 respectively for the transformer and MLP weights respectively.

Design by adaptive sampling (DbAS) is described in "Design by Adaptive Sampling" by Brookes et al., 2018 (hereinafter "Brookes"), which is hereby incorporated by reference in its entirety. In the present disclosure, in some embodiments, DbAS is employed to iteratively generate proteins with decreased immunogenicity while retaining function compared to an input or sampled protein or protein sequence. DbAS begins by sampling a set of proteins that perform the desired function to train an initial generative model. Given a set of training items X drawn from an underlying sample, a generative model learns the underlying distribution P(X). After training, the generative model can sample from P(X) to produce items similar to those in the training set, but not actually in the training set. In other words, the generative model generates new items that are unique and distinct from the training set. In this case, the trained model generates proteins that perform the same function as the training proteins, but are different from the training proteins (e.g., the set of sampled proteins).

Each successive iteration of DbAS, retrains the generative model with items sampled from the previous generator. Predictions from an oracle are used to weight the importance of each item to shift the generative model towards items that fulfill certain criteria (e.g., minimizing immunogenicity), The oracle is a probabilistic black-box function $f(X)$ that returns a probability distribution over the properties of interest (e.g., function, immunogenicity). The items generated by the previous iteration of the generative network are then weighted by the probability that they will be above a $Q_{th}$ percentile in the current iteration for the property of interest. Q is a hyperparameter set by a user. Therefore, each iteration of the generator should produce samples that are more likely to fulfill the desired criteria by weighting above the $Q_{th}$ percentile each iteration.

In other embodiments, Gradient Based Design (GBD) and Computational Directed Evolution (CDE) can be used in place of or as a supplement to DBAS.

In a simplified example, consider the above process where the set of sampling inputs 202 are circles having a variety of colors. FIG. 2A is a diagram 200 illustrating an embodiment of this simplified example. First, the process trains a generator 204 (e.g., the generative network's encoder and decoder) to produce circles using the set of sampling inputs 202. The generator includes an encoder 226 that maps the sampling inputs 202 to a latent vector 207. A decoder 228 then attempts to reconstruct the input from the latent vector 207 to produce an output. In the training example illustrated in diagram 200, the circles of the sampling inputs 202, which are colored green, light blue, gray, dark blue, orange, and yellow, are the same as the outputs of the decoder 208, which are also colored green, light blue, gray, dark blue, orange, and yellow. The encoder 207 and decoder 208 together make up the generative network 204. The encoder 207 produces the latent vector that is passed to the decoder 208.

Second, suppose the user wants to produce more circles of a particular color, for example, red. FIG. 2B is a diagram 220 illustrating such an example embodiment. Such sampling inputs 222 can be expressed by setting Q as a certain "level" of red. A person having ordinary skill in the art can recognize that the sampling inputs 222 are weighted higher for red coloring by providing 4 red circles, 2 pink circles, and only 1 green, light blue, and yellow. The user can input the desire to upweight redder circles (e.g., setting circle color at or above Q or "above the $Q_{th}$ percentile"), train a new generative network 204 with these inputs 222 (including encoder 226, latent vector 227, and decoder 228), and then produce redder circles as output. After several iterations of retraining, the generator produces circles that are much redder than the original sample when decoding 228 the latent vector.

FIG. 3A is a diagram 300 illustrating the original training set 300, which includes circles colored green, light blue, gray, dark blue, orange, and yellow, as also illustrated in FIG. 2A. FIG. 3B is a diagram 310 illustrating the samples after 1 iteration of setting Q to be a redder color. In this output, the colors are yellow, orange, magenta, light red, and red. FIG. 3C is a diagram 320 illustrating the samples after 2 iterations of setting Q to be a redder color. In this output, the colors are all varying shades of red.

In the example described in relation to FIGS. 2A-B and 3A-C, the neural network is trained to generate circles of a different color to describe the concepts of the present disclosure. The system and methods disclosed herein include training a neural network based on protein sequences known to have certain properties, such that the neural network generates more protein sequences having a high likelihood of having those properties. In addition, the neural network can generate protein sequences having a high likelihood of having the functionality of the sample sequences, while also having other properties, such as a low immunogenicity score. Embodiments of method and system of building, training, and using such a neural network are described below.

In example embodiments, the generator and its components are described below. In one example embodiment, the generative model is a variational autoencoder. Following Brookes, a variational autoencoder (VAE) for the generative model is employed. "Auto-Encoding Variational Bayes" by Kingma (available at https://arxiv.org/abs/1312.6114) (hereinafter "Kingma") discloses an example of a VAE. A VAE includes an encoder and a decoder, both of which are neural networks. The encoder $q_\theta(z|x)$ maps an input x to a latent vector z using parameters $\theta$. The encoder is stochastic: it outputs parameters to $q_\theta(z|x)$, which is a Gaussian probability density. Sampling from this distribution can generate noisy realizations of z.

The decoder $p_\phi(x|z)$ attempts to reconstruct the input from z using parameters $\phi$. The encoder and decoder are trained end-to-end to minimize the negative log-likelihood of the reconstruction and the Kullback-Leibler-divergence (hereinafter "KL divergence") between $q_\theta(z|x)$ and Normal(0,1). That is, the loss for data point $x_i$ is represented by:

$$l_i(\theta,\phi) = -E_{z \sim q_\theta(z|x_i)}[\log p_\phi(x_i|z)] + KL[q_\theta(z|x_i) \| \text{Normal}(0,1)]$$

The loss represents the quantity the VAE attempts to minimize during its training. The log-loss encourages accurate reconstruction, while the KL-divergence acts as a regularizer that encourages the latent vectors to be compact. In machine learning, regularization is the process of adding information to a problem to constrain the allowable solutions or to prevent overfitting. Therefore, a regularizer is a module that performs regularization.

In an embodiment, the method aligns the original training set of protein sequences, and then represents each sequence using one-hot vectors. A person having ordinary skill in the art can recognize that a one-hot vector (or one-hot encoding) is a 1×N vector with all low (0) bits except a single high (1) bit. In one-example, the one-hot vector can represent a particular amino acid of the protein sequence with its "hot" bit. The method trains the VAE to reconstruct the one-hot representation of each protein. Both the encoder and decoder are feed-forward neural networks with two hidden layers of size 1024. The latent representation has 512 dimensions.

In an embodiment, the oracle of the present disclosure should provide a measure of immunogenicity. One oracle of the neural networks can include NetMHCIIpan, which is an MHC II predictor and a neural-network based model. Another example of such an oracle of the neural networks is MHCFlurry, which is an MHC I predictor itself is a neural-network based model. MHCFlurry is described in further detail in MHCFlurry: Open-source class MHC Binding Affinity Prediction by Timothy O'Donnell et al., which is available at https://www.cell.com/cell-systems/fulltext/S2405-4712(18)30232-1, and hereby incorporated by reference in its entirety. The oracle predicts the binding affinity between arbitrary amino-acid k-mers and a specified allele (e.g., a MHC I or MHC II allele). Examples of such alleles are those from balbc and C57BL6 mice, such as HLA-DRB1*01:01 and H-2-IAd. A person having ordinary skill in the art can recognize that other oracles for predicting interactions with the same or other immune system molecules may be used to predict other affinities, functions, immunogenicities, or other desired protein sequence properties can be employed. A person of ordinary skill in the art can also recognize that the oracle includes and utilizes a set of supported alleles, such as those listed in Appendix A and are hereby incorporated by reference into this application. A person having ordinary skill in the art recognizes that the list of alleles in Appendix A are known and can be identified in allele databases.

In the case of MHC I, the predicted binding affinities of a protein's constitutive 9-mers to the MHC I allele are a measurement of immunogenicity. MHCFlurry returns binding affinities for each 9-mer in a protein. The method can combine the binding affinities generated by the oracle (e.g., MHCFlurry) into one immunogenicity score K for each protein:

$$K(p) = (\Sigma 1 K_i)_{-1}$$

where $K_i$ represents the binding affinities for each 9-mer in the protein p. Note that a higher K denotes weaker binding and therefore lower immunogenicity. A person having ordinary skill in the art can recognize that other summarization functions, such as the maximum, can be used to summarize residue- or peptide-level scores across a protein to produce a single protein K score. When using an MHC II oracle such as NetMHCIIpan, 15-mers can be more viable than 9-mers, as well as other differences known to a person of ordinary skill in the art.

Therefore, the K scores, as described above, can be used as Q levels. Much like the example described above, where Q sets a desired level of "redness" of the generated circles, in the present disclosure, Q can be set to a certain level of K, where the model attempts to find protein sequences with weaker and weaker predicted binding affinities.

In embodiments, the method adds further constraints on the sequences sampled at each iteration to help maintain protein function. First, the method rejects samples falling outside the length distribution for the original training set. In other words, generated samples that fall outside of a standard deviation, or other statistical measure, of the input set of proteins, are rejected and not used for retraining the model.

Second, an annotator trained on UniProt and/or a function predictor trained on experimental data rejects sequences that are unlikely to be functional. A person having ordinary skill in the art can recognize that another function can also provide likelihood of protein functionality.

Third, the method rejects sampled sequences where the fraction of the sequence consisting of repeats is greater than some cutoff, which helps avoid regions of the latent space where the generator has not converged.

In the above embodiments, the system and method describe employ a VAE, however, other generative models can be employed. In embodiments, generative models that can be trained with sequence information only, sampled, and retrained in a DBAS loop can be employed. Other types of generative models that can be employed include, but are not limited to, (1) a first order model of per-residue AA probabilities (also known as probability weight matrix, PWM, position-specific scoring matrix, PSSM), (2) a second order model of per-residue AA probabilities and residue-residue interaction probabilities (aka Potts model, Ising model, Markov Random Field), (3) a generative adversarial network (GAN), (4) an energy-based model of overall sequence probability that is derived from a classifier (e.g., with transformer and CNN architectures), and (5) autoregressive language model (LM) or masked language model (MLM) (e.g. self-supervised learning using transformer or recurrent neural network architecture).

In an example embodiment, accuracy information is provided for the VAE on the original dataset and metrics for sequences generated using DbAS. In one embodiment, 7000 β-lactamases were explored. After eliminating sequences having lengths less than 200 or more than 600, 20% of the remaining sequences were randomly held out as a validation set and the remainder were used to train the prototype VAEs. The average validation accuracy for the VAE described above was 88.2%.

The full dataset then trained the initial generator for DbAS. During DbAS, sequences with a repeat fraction greater than 0.05 or a probability less than 0.8 of having one of 4 Pfam annotations associated with β-lactamases were rejected. Over 15 iterations of DbAS, the method found sequences that more than doubled K while maintaining a high probability of being a β-lactamase, as predicted by the Pfam annotator.

In another example embodiment, a second humanization was performed with a set of 1026 β-lactamases with experimentally-confirmed activity against cefoxitin or a predicted probability >0.35 of activity against cefoxitin. Twenty percent (20%) of these were randomly held out as a validation set and the remainder trained the prototype VAEs. The average validation accuracy for the VAE described above was 95.6%.

The full cefoxitin dataset then used to train the initial generator for DbAS. During DbAS, sequences with a repeat fraction greater than 0.05, a predicted probability less than 0.35 of activity towards cefoxitin, or a predicted probability less than 0.7 of belonging to one of 4 β-lactamase Pfam annotations for beta-lactamase domains were rejected. Over 15 iterations of DbAS, sequences were found that approximately doubled K while maintaining a high probability of being a β-lactamase, as predicted by the Pfam annotator.

In an embodiment, 12583 sequences with the InterPro label IPR004550 (Asparaginase Type II) were explored using the disclosed method. The method eliminated sequences with length less than 300 or more than 380, and then the method greedily removed sequences to shorten the alignment length. The final training set includes 8972 sequences. 20% of these were randomly held out as a validation set and the remainder trained the prototype VAEs. The average validation accuracy for the VAE described above was 86.0%.

The full filtered dataset then trained the initial generator for DbAS. During DbAS, sequences with a repeat fraction greater than 0.05 or a probability less than 0.95 of having Pfam annotation PF00710, as predicted by a neural network, were rejected. Over 25 iterations of DbAS, sequences were found that approximately doubled K while maintaining a high probability of being an asparaginase, as predicted by the Pfam annotator.

100 selected asparaginase sequences are optimized for low MHCII presentation by this method and assayed their enzymatic activity in-house. Sequences were selected based on the maximum probability of MHCII presentation across all 15-mer peptides in each protein as predicted by the model (called "stealth score" in Figure X). This probability was high for the wild type *E. coli* and *Erwinia* asparaginases used in the clinic. MHCII presentation probability for our generated variants, however, were well below those of *E. coli* and *Erwinia* enzymes. Furthermore, all sequences were very divergent from the training set, with high-confidence sequences having in the range of 40-80 mutations from the closest natural sequence, and low-confidence sequences in the range of 100-160 mutations. Figure X shows experimental validation of enzymatic activity for these novel stealth asparaginases.

Next, the method produced high amounts of purified protein from 10 of these active enzymes for in vivo validation of immune evasion in a mouse model. Mice were injected with either the *E. coli* wild type asparaginase or one of generated asparaginases optimized for low predicted MHCII presentation. Serum was drawn at multiple timepoints after injection and anti-drug antibody (ADA) titers were assayed for each enzyme. As Figure Y shows, the generated asparaginase sequences elicited lower ADA levels than the *E. coli* asparaginase at all timepoints. Further, two of the novel proteins had no detectable ADAs even at 21 days.

FIG. 8 illustrates a computer network or similar digital processing environment in which embodiments of the present invention may be implemented.

Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 9:
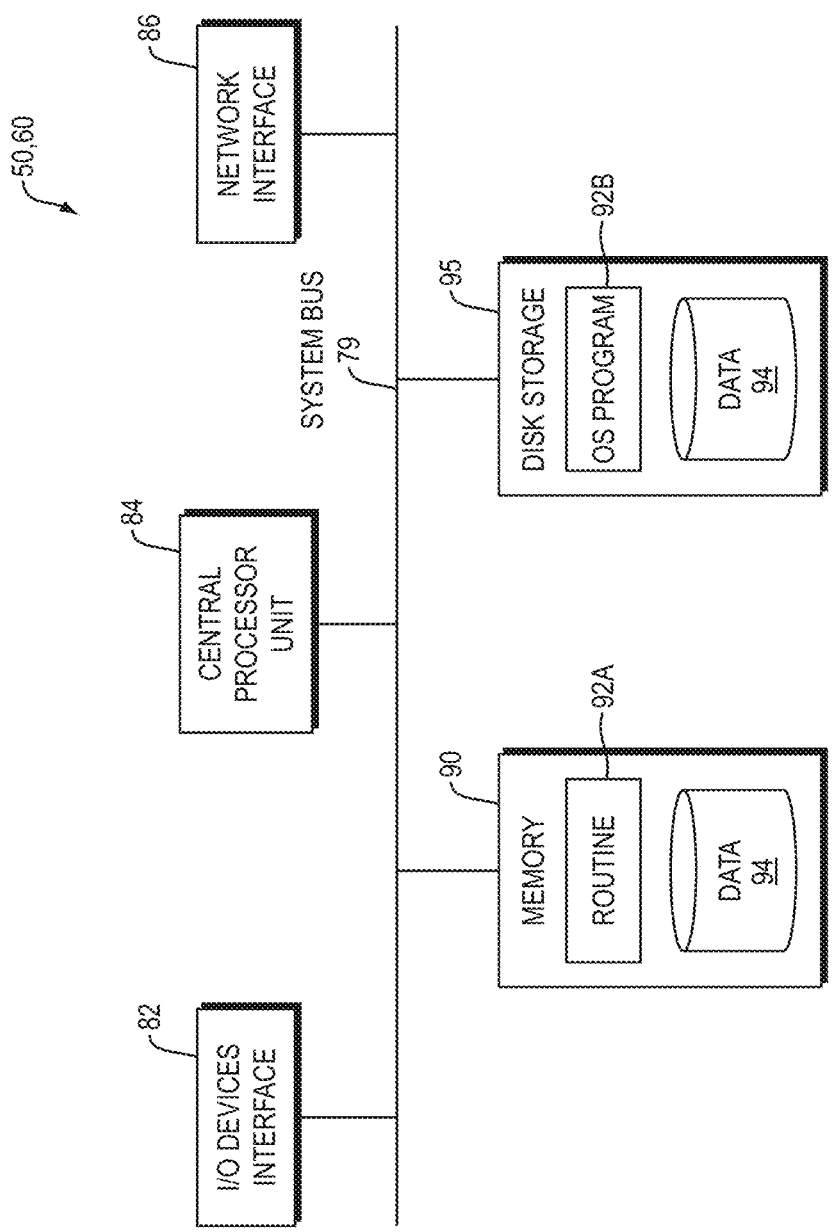
FIG. 9 is a diagram of an example internal structure of a computer (e.g., client processor/device or server computers) in the computer system of FIG. 8 according to an exemplary embodiment of the present disclosure.

FIG. 9 is a diagram of an example internal structure of a computer (e.g., client processor/device 50 or server computers 60) in the computer system of FIG. 8. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 5). Memory 90 provides volatile storage for computer software instructions 92 and data 94 used to implement an embodiment of the present invention (e.g., neural network module, generator module, encoder module, and decoder model code detailed above). Disk storage 95 provides non-volatile storage for computer software instructions 92 and data 94 used to implement an embodiment of the present invention. A central processor unit 84 is also attached to the system bus 79 and provides for the execution of computer instructions.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals may be employed to provide at least a portion of the software instructions for the present invention routines/program 92.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of generating a sequence of a protein predicted to have altered immunogenicity compared to a sampling of protein sequences, the protein having a desired function, comprising:
    evaluating the immunogenicity of a sampling of protein sequences;
    selecting a set of protein sequences from the sampling by weighting the sampling of protein sequences according to an estimated probability of a particular generated protein sequence having a deviation in immunogenicity of a particular percentile of immunogenicity of the sampling of protein sequences, wherein the sampling of protein sequences is from a generative model and the generative model is configured to preserve the desired function; and
    generating a protein sequence based on the selected set of protein sequences, the protein sequence representing a protein predicted to have an altered immunogenicity, wherein the evaluating includes using residue-wise predictions of a relative likelihood for MHC II to bind to the protein predicted to have the altered immunogenicity, and wherein the altered immunogenicity is reduced immunogenicity that improves a likelihood of humanization relative to the immunogenicity of the sampling of protein sequences.

2. The method of claim 1 further comprising:
    retraining the generative model based on the selected set of protein sequences;
    wherein generating the protein sequence is based on the retrained generative model that is retrained based on the selected set of protein sequences.

3. The method of claim 2, further comprising:
    retraining the generative model two or more iterations, wherein each iteration includes:
    a) evaluating the immunogenicity of a sampling of protein sequences generated by the retrained generative model, and
    b) further retraining the generative model by weighting the sampling of protein sequences generated by the retrained generative model according to their evaluated immunogenicity in the retraining.

4. The method of claim 2, wherein the sampling of protein sequences is unique from any protein sequences present in a training set of protein sequences used to train the generative model.

5. A method of generating a sequence of a protein predicted to have altered immunogenicity compared to a sampling of protein sequences, the protein having a desired function, comprising:
    evaluating the immunogenicity of a sampling of protein sequences;
    weighting the sampling of protein sequences according to an estimated probability of a particular generated protein sequence having a deviation in immunogenicity of a particular percentile of immunogenicity of the sampling of protein sequences, resulting in a first weighted sampling of protein sequences;
    evaluating the immunogenicity of a sampling of protein sequences using first sampling of protein sequences;
    reweighting the sampling of protein sequences from the first weighted sampling of protein sequences evaluated for immunogenicity according to their evaluated immunogenicity, resulting in a second weighted sampling of protein sequences;

generating a protein sequence from the second weighted sampling of protein sequences, the protein sequence representing a protein predicted to have an altered immunogenicity; and providing a generative model that preserves the desired function, the generative model comprising an encoder neural network and a decoder neural network, wherein immunogenicity is evaluated using residue-wise predictions of a relative likelihood for MHC II to bind to the protein predicted to have the altered immunogenicity, and wherein the altered immunogenicity is reduced immunogenicity that improves a likelihood of humanization relative to the immunogenicity of the sampling of protein sequences.

6. The method of claim 5, wherein evaluating the immunogenicity of the sampling of protein sequences further includes evaluating the immunogenicity from a generative model, wherein the generative model preserves the desired function, the generative model further comprising an encoder neural network and a decoder neural network.

7. The method of claim 5, wherein the sampling of protein sequences does not comprise any protein sequences present in a training set of protein sequences used to weight the first weighted sampling of protein sequences, and the first weighted sampling of protein sequences does not comprise any sequences present in a training set of protein sequences used to weight the first weighted sampling of protein sequences.

8. The method of claim 5, further comprising iterating the steps of evaluating the immunogenicity of a sampling of protein sequences and reweighting the sample of protein sequences, resulting in a second weighted sampling of protein sequences.

9. The method of claim 5, wherein immunogenicity is evaluated using the predicted affinity of k-mers of a subject sequence for a MHC molecule.

10. The method of claim 9, wherein k is greater than or equal to 5 and less than or equal to 13.

11. The method of claim 9, wherein the predicted affinity for a k-mer of a subject sequence for the MHC molecule is evaluated by one or more of MHCFlurry, NetMHCpan, or NetMHCIIpan.

12. The method of claim 9, further comprising combining the predicted affinity of k-mers by at least one of (a) the reciprocal of the sum of the reciprocal of each predicted affinity of k-mers, and (b) the lowest predicted affinity of the k-mers.

13. The method of claim 5, wherein the immunogenicity of the sampling of protein sequences from the first weighted sampling of protein sequences or second weighted sampling of protein sequences is evaluated experimentally.

14. The method of claim 5, wherein the altered immunogenicity is one or more of increased affinity and reduced affinity for a human MHC, including at least one of human MHC I, wherein the human MHC I is encoded by allele HLA-A0201, and MHC II.

15. The method of claim 5, wherein the desired function is selected from enzymatic activity, asparaginase activity, target binding affinity (other than an MHC), thermal stability, solubility, size of protein, intracellular location of protein, activation of a cellular signaling pathway or gene expression program, and expression level.

16. The method of claim 5, wherein a candidate model accepts an amino acid sequence as input and outputs one or more residue-wise predictions of relative likelihood for MHCII to bind to a peptide containing each residue.

17. The method of claim 5, wherein the estimated probability is a likelihood of MHC II presentation, and the likelihood is based on a probability of peptide presentation of MHC-associated peptide proteomics (MAPPS).

18. The method of claim 5, wherein the first weighted sampling of protein sequences is used to provide a first updated generative model by updating a generative model, and second weighted sampling of protein sequences is used to provide a second updated generative model that retrains the first updated generative model.

19. A method of generating a sequence of a protein predicted to have altered immunogenicity compared to a sampling of protein sequences, the protein having a desired function, comprising:

evaluating the immunogenicity of a sampling of protein sequences from a generative model, wherein the generative model preserves the desired function, the generative model further comprising an encoder neural network and a decoder neural network, wherein the encoder neural network and decoder neural network were trained to minimize (i) a negative log-likelihood of a reconstruction of an input to the encoder by an output of the decoder or (ii) a Kullback-Leibler-divergence (KLD) between the encoder and Normal (0,1);

providing a first updated generative model by retraining the generative model by weighting the sampling of protein sequences from the generative model according to an estimated probability of a particular generated protein sequence having a deviation in immunogenicity of a particular percentile of immunogenicity of the sampling of protein sequences;

evaluating the immunogenicity of a sampling of protein sequences using the first updated generative model;

providing a second updated generative model by retraining the first updated generative model by weighting the sampling of protein sequences from the first updated generative model evaluated for immunogenicity according to their evaluated immunogenicity in the retraining; and generating a protein sequence from the second updated generative model, the protein sequence representing a protein predicted to have an altered immunogenicity, wherein the altered immunogenicity improves a likelihood of humanization relative to the immunogenicity of the sampling of protein sequences.

20. The method of claim 19, wherein the generative model was trained using a set of naturally occurring sequences predicted to have the desired function.

21. The method of claim 19, wherein the encoder neural network and decoder neural network employ at least two hidden layers.

22. The method of claim 19, wherein a neural network of the generative model evaluates the immunogenicity of the sampling of protein sequences by an oracle outputting at least one of a value and an uncertainty.

* * * * *